United States Patent
Font Perez et al.

(10) Patent No.: US 8,685,732 B2
(45) Date of Patent: Apr. 1, 2014

(54) BIOMATERIAL BASED ON WHARTON'S JELLY FROM THE HUMAN UMBILICAL CORD

(75) Inventors: Julio Font Perez, Bilbao (ES); Maite Del Olmo Basterrechea, Sopelana (ES); Maria Begona Castro Feo, Leioa (ES); Arantza Infante Martinez, Algorta-Getxo (ES); Ana Isabel Alonso Varona, Getxo (ES); Teodoro Palomares Casado, Vitoria (ES)

(73) Assignee: Histocell, S.L., Derio (ES)

( * ) Notice: Subject to any disclaimer, the term of this patent is extended or adjusted under 35 U.S.C. 154(b) by 91 days.

(21) Appl. No.: 13/123,186

(22) PCT Filed: Oct. 10, 2008

(86) PCT No.: PCT/ES2008/000640
§ 371 (c)(1),
(2), (4) Date: Jun. 9, 2011

(87) PCT Pub. No.: WO2010/040865
PCT Pub. Date: Apr. 15, 2010

(65) Prior Publication Data
US 2011/0256186 A1    Oct. 20, 2011

(51) Int. Cl.
*C12N 5/00* (2006.01)
*C12N 5/02* (2006.01)
*A61F 2/02* (2006.01)

(52) U.S. Cl.
USPC ....... 435/395; 435/325; 424/93.7; 424/93.71; 424/426

(58) Field of Classification Search
None
See application file for complete search history.

(56) References Cited

U.S. PATENT DOCUMENTS 5,919,702 A * 7/1999 Purchio et al. ................ 435/378

FOREIGN PATENT DOCUMENTS

| WO | 99/61080 A1 | 12/1999 |
| WO | 2008/021391 A1 | 2/2008 |

OTHER PUBLICATIONS

Bankowski "Collagen and glycosaminoglycans of Wharton's jelly and their alterations in EPH-gestosis" European Journal of Obstetrics and Gynecology and Reproductive Biology, 1996, 66, 109-117.*
Viscosity Chart, "Viscosity Chart", 2001, available at www.research-equipment.com/viscosity%20chart.html, web-capture indicating webpage available from Jan. 2001 included.*
Krzysztof Sobolewski, et al., "Collagen and Glycosaminoglycans of Wharton's Jelly", Biology of the Neonate, 1997, pp. 11-21, vol. 71, pp. 11-21.
R.E. Baier, "Advanced Biomaterials Development from "Natural Products"", Journal of Biomaterials Applications, Apr. 1988, pp. 615-626, vol. 2.
International Search Report PCT/ES2008/000640, Jun. 29, 2009.

* cited by examiner

*Primary Examiner* — Jon P Weber
*Assistant Examiner* — Charles Zoltan Constantine
(74) *Attorney, Agent, or Firm* — Sughrue Mion, PLLC

(57) ABSTRACT

The present invention relates to a biomaterial, specifically a hydrogel, formed from the extracellular matrix of the umbilical cord for its application in regenerative medicine. The invention particularly relates to a biomaterial made up of glycosaminoglycans isolated exclusively from the Wharton's jelly of the umbilical cord which can optionally contain cells, and also to the methods for the production and use thereof.

19 Claims, 5 Drawing Sheets

BIOMATERIAL BASED ON WHARTON'S JELLY FROM THE HUMAN UMBILICAL CORD

CROSS REFERENCE TO RELATED APPLICATION

This application is a National Stage of International Application No. PCT/ES2008/000640 filed Oct. 10, 2008, the contents of all of which are incorporated herein by reference in their entirety.

TECHNICAL FIELD OF THE INVENTION

The present invention relates to a biomaterial, specifically a hydrogel, formed from the extracellular matrix of the umbilical cord for its application in regenerative medicine. The invention particularly relates to a biomaterial made up of glycosaminoglycans isolated exclusively from Wharton's jelly of the umbilical cord which can optionally contain cells, and also to the methods for the production and use thereof.

BACKGROUND OF THE INVENTION

The biomaterials formed by polymers play a central role in regenerative medicine since they provide temporary three-dimensional anchors for the adhesion, proliferation and the differentiation of transplanted cells. This three-dimensional nature provides a suitable platform for intercellular communication and the relationship of the cells with the components of the biomaterial. The biointeraction occurring between the matrix and the cells over time determines the proliferative capacity of the cells, their organization for the formation of a new tissue, their differentiation and the secretion of signaling molecules which direct the regenerative process (Dawson et al., 2008).

In order for these phenomena to occur, it is necessary for the biomaterial to remain in the site of application for a limited time until its reabsorption, conserving its structure long enough for a suitable cellular action with regenerative consequences.

A specific type of biomaterial, hydrogels, has a number of properties that make them suitable for their application in tissue engineering.

Hydrogels are structures formed by interconnected hydrophilic polymers of a natural or synthetic nature, with the capacity to contain a large amount of water inside their structure, from 10-20% up to hundreds of times their own weight. These gels show a semi-solid morphology the three-dimensional lattice of which is presented as an ideal candidate for forming a structural matrix capable of acting as a support. This three-dimensional structure can be formed by both physical crosslinking and by chemical crosslinking. Physical crosslinking leads to reversible hydrogels the structure of which can be reversed according to the end application, whereas chemical crosslinking leads to permanent hydrogels the structure of which will be maintained through the entire application (Coburn et al., 2007). Therefore, hydrogels are polymer materials (of a natural or synthetic nature) crosslinked in the form of a three-dimensional network which swell in contact with water, forming soft elastic materials, and which retain a significant fraction thereof in their structure without dissolving.

Hydrogels have a series of particular characteristics, such as:

1. Hydrophilic nature: due to the presence in their structure of water-soluble groups (—OH, —COOH, —CONH2, —CONH, SO3H). They have a high water content similar to that of live tissues (Elisseeff et al., 2005).
2. Insoluble in water: due to the existence of a three-dimensional polymer network in their structure.
3. They have a smooth and elastic consistency which is determined by the hydrophilic starting monomer and the low crosslinking density of the polymer.

They have the capacity to swell in the presence of water or aqueous solutions, considerably increasing their volume until reaching a chemical-physical equilibrium, but without losing their form. This capacity to swell provides an aqueous microenvironment comparable to that which the cells are subjected in soft tissues. The presence of water and of a porous structure also allows the flow of low molecular weight solutes and of nutrients that are crucial and essential for cell viability, as well as the transport of cell wastes outside the hydrogel (Torres et al., 2000).

The umbilical cord is a highly vascularized structure with an important cell component. The cells and the vascular system are integrated in a gelatinous connective tissue called Wharton's jelly (WJ). WJ contains a low amount of cells and high levels of extracellular matrix, primarily made up of collagen, hyaluronic acid and sulfated glycosaminoglycans.

Glycosaminoglycans (GAGs), also referred to as mucopolysaccharides, are heteropolysaccharides found in organisms bound to a protein nucleus forming macromolecules referred to as proteoglycans. These can be found on the surfaces of cells or in the extracellular matrix and carry out important functions for cell-cell and cell-extracellular matrix interactions. They are in sulfated and non-sulfated form and the common characteristic of these molecules is their composition in a repeated sequence of disaccharides formed by two different sugars: one of them is usually a hexuronate while the other one is a hexosamine. The configurational variation in the bonding of the disaccharides and the position of sulfation leads to an increase of the diversity in the physical and chemical properties of these chains. The high sulfate content and the presence of uronic acid confers to GAGs a large negative charge, so the large amount of GAGs in WJ make this tissue be extremely hydrated.

There are several types of GAGs, which are directly involved in basic cell functions, not only due to their structure, but also because they are anchor sites for several cell signaling molecules.

Hyaluronic acid is the most abundant GAG in WJ. It is the only non-sulfated member of the GAG family which functions in vivo like a free carbohydrate, its structure consisting of repeats of a disaccharide: D-glucuronic acid and (1-$\beta$-3) N-acetyl-D-glucosamine (Goa et al., 1994; Laurent et al., 1992). It is synthesized by several cell types and is secreted into the extracellular space where it interacts with other components of the extracellular matrix to create the support and protection structure surrounding the cells (Collins et al., 2008). It is a large, polyanionic linear polymer, and a single molecule can have a molecular weight of 100,000 to $5.10^6$ Da (Toole et al., 2004; Bertolami et al., 1992). It has a coiled structure taking up a large volume, leading to high viscosity solutions. The individual molecules of hyaluronic acid associate with one another, forming networks or lattices. In developing tissues, hyaluronic acid is considered the main structural macromolecule involved in cell proliferation and migration.

Hyaluronic acid has been involved in several processes, such as vascularization, morphogenesis, general integrity and repair of the extracellular matrix. It is known that a large amount of hyaluronic acid contained in amniotic fluid favors the repair of fetal wounds (Longaker et al., 1989). Variations in its molecular properties between healthy skin and scars have furthermore been observed, hyaluronic acid of normal scars certainly being different from that of hypertrophic scars (Ueno et al., 1992).

Chondroitin sulfate is a linear polymer formed by a D-glucuronic acid dimer and N-acetylgalactosamine repeat. Its usefulness has been tested in therapies targeted against joint diseases by means of inhibiting the activity of the enzymes responsible for the degradation of the matrix of the cartilage components. It would also act as an anti-inflammatory by means of the inhibition of the complement and is useful in the treatment of thromboembolic disorders, in surgery and opthalmological clinics.

Dermatan sulfate, also known as chondroitin sulfate B, is a potent anti-coagulant due to its selective inhibitory effect on thrombin through heparin cofactor II, being very effective in vivo due to its lower hemorrhagic risk (Trowbridge et al., 2002).

Glycosaminoglycans in general, and heparin in particular, have the capacity to modulate plasma cascade activity, enhancing the inhibition of the intrinsic coagulation pathway and inhibiting the classic complement activation pathway at different points (Rabenstein, 2001). Other known functions of the heparin are the inhibition of angiogenesis, humoral growth and its antiviral activity.

Heparan sulfate has a structure that is closely related to heparin. It is widely distributed in animal tissues and among its functions, cell adhesion and the regulation of cell proliferation stand out. It has a protective effect against the degradation of proteins, regulating their transport through the basement membrane and also intervening in the internalization thereof (Rabenstein, 2001).

There are several patent documents relating to mucopolysaccharides obtained from human or animal origin. Document U.S. Pat. No. 3,887,703 relates to mixtures of mucopolysaccharides obtained from the cutaneous teguments and umbilical cords of the fetus of a cow or sheep. The only example that uses an umbilical cord is of a cow fetus 1-9 months old and it does not mention that the membrane or the vessels are eliminated since the first operation is grinding under 10° C. The individual mucopolysaccharides forming the mixtures or the amounts present are not mentioned; the active products are identified by the amount of hexosamines that are present in the mixture. Compositions in both injectable and oral ingestion forms for the treatment of oily scalp and hair and for inflammations are prepared with the extracts.

Patent document U.S. Pat. No. 5,814,621 relates to a composition essentially consisting of a drug which is more soluble in an organic solvent-water mixture than in water, and a mucopolysaccharide forming part of a drug, in which crystals or particles of the drug are distributed on the surface of the particles of the mucopolysaccharide and in which said drug dissolves in water more quickly than if it were alone. Said composition can be in the form of granules.

Patent application WO 2008/021391 A1 describes biomaterials comprising the umbilical cord membrane. Furthermore, it can additionally comprise one or more umbilical cord vessels and/or Wharton's jelly. The biomaterial is preferably dry and can be flat, tubular or shaped to fit a particular structure. The invention also provides methods of making the biomaterial comprising at least one layer of the umbilical cord membrane, as well as the methods for obtaining said biomaterials and the use thereof for repairing tissues or organs.

The description characterizes the biomaterial from the umbilical cord. It describes that the composition of said material comprises collagen (type I, III and IV, these being 75-80% of the percentage of the matrix of the biomaterial), fibronectin and glycosaminoglycans.

It is also mentioned that the biomaterial can also comprise collagen that does not come from umbilical cords and has a commercial origin, or it has been isolated from other tissues and methods known in the state of the art. The authors also add that the biomaterial can comprise non-structural compounds such as growth factors, hormones, antibiotics, immunomodulatory factors, etc.

Spanish patent ES 8600613 describes a process for the treatment of body tissues, for separating cell membranes, nucleic acids, lipids and cytoplasmic components and forming an extracellular matrix the main component of which is collagens, and for making the body tissue suitable for being used as a body graft, comprising extracting said tissue with at least one detergent while at the same time it is maintained with a size and shape suitable for the grafting thereof in the body.

Patent document ES 2 180 653 T3 describes methods for transforming biological materials into substances which have experienced autolysis for eliminating at least 70% of the cells and methods for the treatment of said material for inhibiting its mineralization after implantation in a human or animal. It claims that the starting biological material can be, among others, the umbilical cord; although it specifically relates to an aortic valve of a pig. Nevertheless, the description does not contain any detail with respect to carrying it out with umbilical cord. The resulting biomaterial is used to create a bioprosthetic heart valve.

Patent document U.S. Pat. No. 4,240,794 relates to preparing human or other animal umbilical cords for their use as a vascular replacement. The document specifically describes a technique for dehydrating the umbilical cord in alcohol followed by a method for fixing it in the desired configuration. It is described that once the umbilical cord has been cleaned of possible remains of other tissues, it is mounted on a mandrel and immersed in a specific ethyl alcohol solution for the time necessary for it to dehydrate. After dehydration, the cord is immersed in a 1% aldehyde solution for fixing.

Patent document FR 2,563,727 describes a method for producing a skin graft from deprogrammed connective tissue impregnated with Wharton's jelly and stored at freezing temperatures. The authors describe a device which is anchored to the umbilical tissue and it is expanded by means of a cannula which injects compressed air. It is described that the umbilical cord is then cut and isolated but the product resulting from this process is not made up of WJ exclusively.

There are patent documents which use umbilical cord to obtain cells of interest, for which purpose they carry out processes for separating Wharton's jelly and eliminating it, thus obtaining said cells. For example, PCT document 98/17791 describes the isolation of pre-chondrocytes from the umbilical cord, which are subsequently used therapeutically to produce cartilage. Similarly, in document WO 2004/072273 A1 progenitor cells are extracted from Wharton's jelly that lies within the perivascular region of the umbilical cord and are used to repair human tissues.

However, there is no document that mentions a biomaterial formed by GAGs located in Wharton's jelly of the human umbilical cord, free of human umbilical cord membrane and blood vessels, which can form a hydrogel that adapts to the necessary viscosity characteristics, etc., to be used in different human pathologies.

Therefore, the biomaterial of the present invention is made up exclusively of the GAGs forming the extracellular matrix of the umbilical cord referred to as WJ. The extracellular matrix is a complex and specific biological substance of tissue. The extracellular matrix derived from blood vessels of the urinary bladder is completely different from that derived from the dermis (Hiles & Hodde, 2006). Thus, although several attempts to synthesize extracellular matrix are known in the literature, an exact composition that simulates the natural conditions of a certain tissue has not been achieved.

The biomaterial developed in the present invention offers a three-dimensional structure which allows the use thereof as a base matrix for tissue engineering and furthermore, when applied directly or with cells, in a pathology, it intervenes in the regenerative process, exerting a call effect on the cells of the tissue itself and providing a favorable environment for the activation of cell processes.

WJ is characterized in that it contains a very low number of cells and, nevertheless, a large amount of extracellular matrix (collagen and GAGs). In other words, the cells found in WJ are highly stimulated and are capable of producing high levels of matrix. This is due to the fact that large amounts of growth factors accumulate in WJ, including transforming growth factor beta (TGF-β), insulin-like growth factor type 1 (IGF-I), fibroblast growth factor (FGF), epidermal growth factor (EGF) and platelet-derived growth factor (PDGF). These growth factors carry out their cell activity regulatory role by means of bonding to specific receptors, some of which are in the various GAGs making up WJ. These growth factors control cell proliferation, differentiation and the synthesis and remodeling of the extracellular matrix forming WJ. The large amount of synthesized matrix provides high mechanical resistance, elasticity and a high hydration capacity which is used to prevent the occlusion of the blood vessels caused by uterine contraction or fetal movements (Sobolewski et al., 2005).

Unlike other biomaterials, the biomaterial of the present invention is made up of a combination of different GAGs from the WJ of the umbilical cord. It is mostly made up of hyaluronic acid, but furthermore, unlike other GAG compounds, it contains dermatan sulfate, heparan sulfate, heparin, keratan sulfate, chondroitin-4-sulfate and chondroitin-6-sulfate. This combination of GAGs improves the bioactivity of the biomaterial, since each of them carries out cell behavior regulatory functions. For example, it is known that heparan sulfate and heparin are the main binding sites for FGF and EGF (Kanematsu et al., 2003; Ishihara et al., 2002), which protect them from proteolysis and allow local concentrations of these factors in the cell environment, creating the molecular microenvironment suitable for large cell activation (Malkowski et al., 2007).

The combination of GAGs present in this biomaterial provides a number of specific signaling molecule binding sites which will allow in the application site high activation of the cells of the tissue itself for the synthesis of high levels of extracellular matrix which will regenerate and repair the treated defect.

Furthermore, the origin of the biomaterial of the invention provides a natural structure of human origin of a non-immunogenic area, the elimination of which is integrated in the normal physiological cycles, which prevents the reactions of the biomaterials of animal origin or the side effects that some synthetic biomaterials may cause, such as inflammation, induration (hardening of organ tissues), onset of granulomas, necrosis in mucosae and tissue complications due to the toxic the substances used in the production thereof.

One of the most important functions of the GAGs in the umbilical cord is to provide strength, elasticity and resistance for protecting the vascular system located therein from external aggressions. In fact, the deficiency in the synthesis of these molecules is involved in important pathologies during pregnancy (Gogiel et al., 2005). Obtaining a biomaterial made up of the 7 different types of GAGs forming part of the umbilical cord would be capable of forming crosslinks between their fibers, simulating what occurs in the organism, and thus providing the strength, elasticity, resistance and compression similar to that conferred in the cord.

The bar chart shows the different types of GAGs present in the biomaterial of the invention, as well as the percentage of each of them therein. HA: hyaluronic acid, KS: keratan sulfate, C6S: chondroitin-6-sulfate, HS: heparan sulfate, C4S: chondroitin-4-sulfate, DS: dermatan sulfate, H: heparin.

Figure 2:
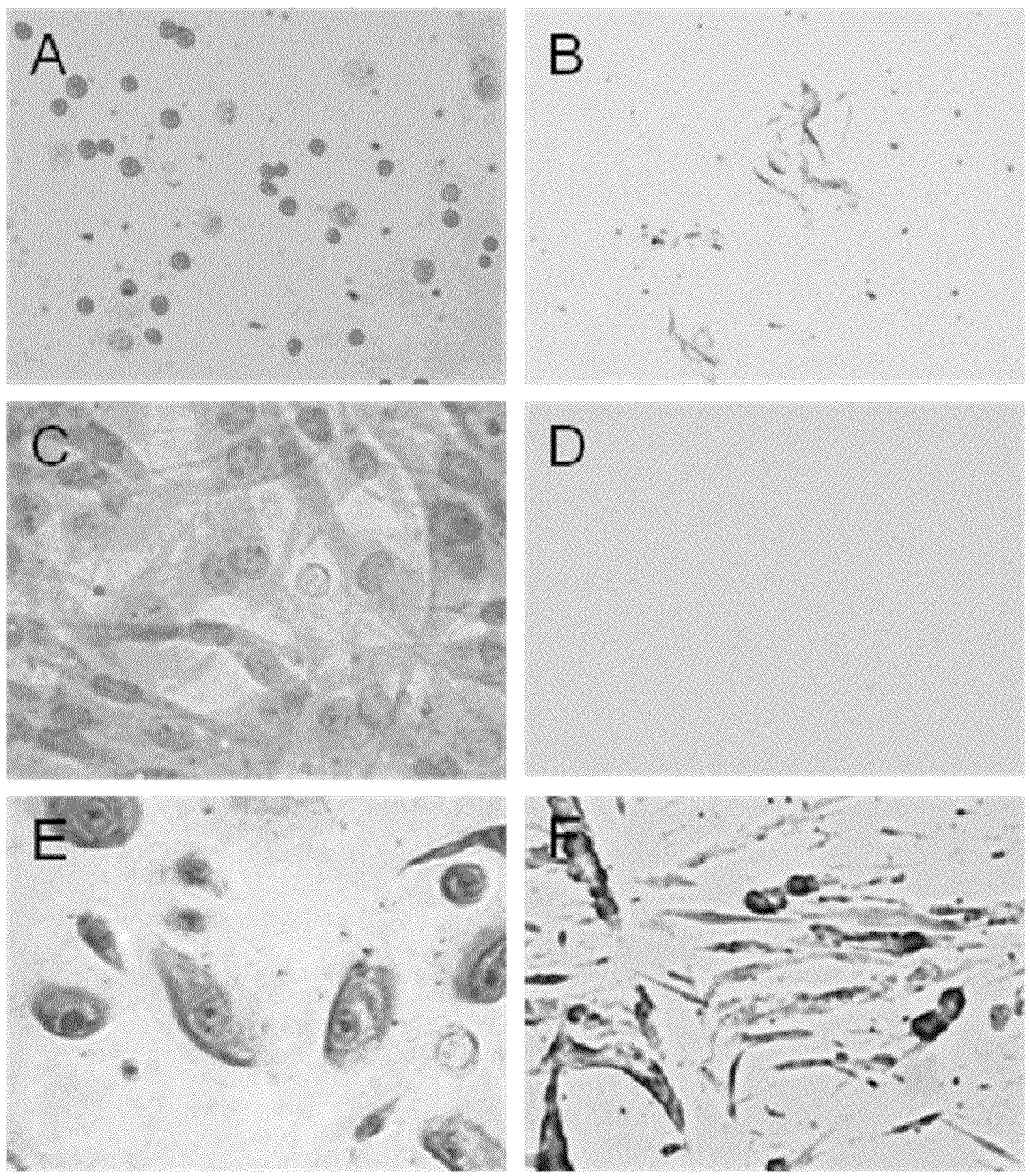

FIG. 2: Verification of the presence of GAGs in the sample and of the absence of cells and DNA/RNA therein by means of histological staining.

The images on the left show the samples with cells and the images on the right show the staining of the biomaterial alone. A, B: hematoxylin-eosin stain; C, D: methyl green-pyronin stain; E, F: alcian blue stain.

Figure 3:
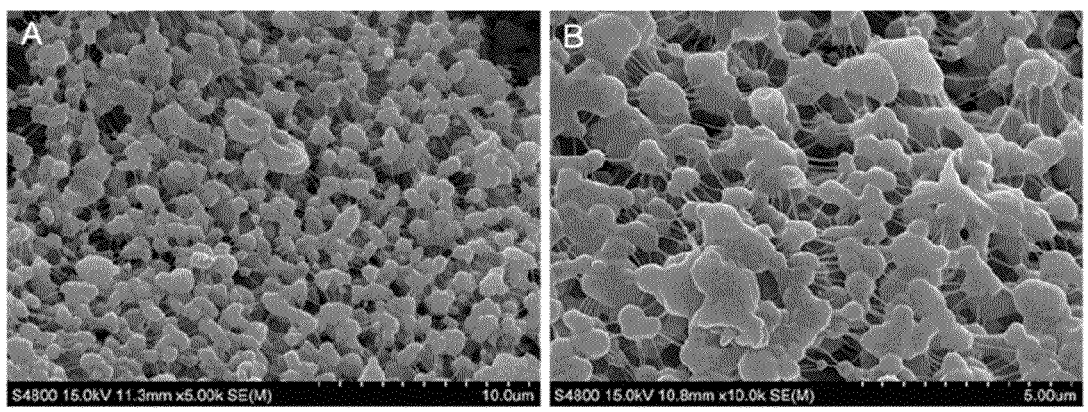

FIG. 3: Images of the internal three-dimensional structure of the biomaterial of the invention by scanning electron microscopy.

The image shows the internal structure of the biomaterial of the invention at two different magnifications (A: 10 μm and B: 5 μm), in which the GAG units interconnected to one another can be seen, offering a very homogeneous porous structure.

Figure 4:
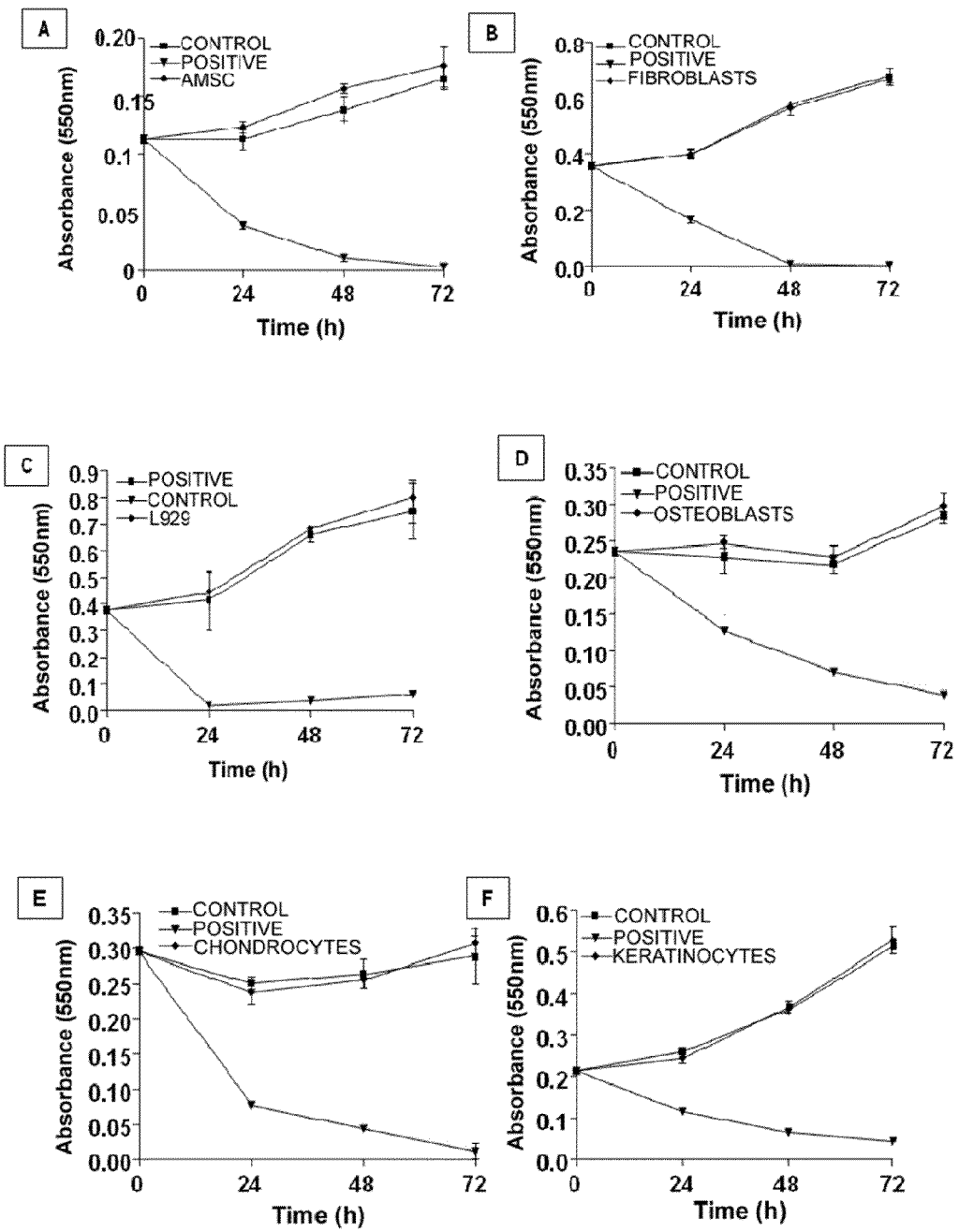

FIG. 4: Results of the toxicity study of the cells in the biomaterial of the invention.

The graphs show the cytotoxicity curves of the AMSC cells (adipose-derived mesenchymal stem cells) (FIG. A), mouse fibroblasts (FIG. B9), L929 (FIG. C), osteoblasts (FIG. D), chondrocytes (FIG. E) and keratinocytes (FIG. F). The results are given with respect to a control (cells without biomaterial) and to a positive control (cells in a toxic biomaterial as determined according to ISO-10993 standard, PVC).

As can be observed in the graphs, the biomaterial does not cause toxicity in any of the tested cell types, since the mitochondrial activity of the cells arranged on the biomaterial does not show differences with respect to the control cells (in standard culture conditions).

Figure 5:
Figure 5:
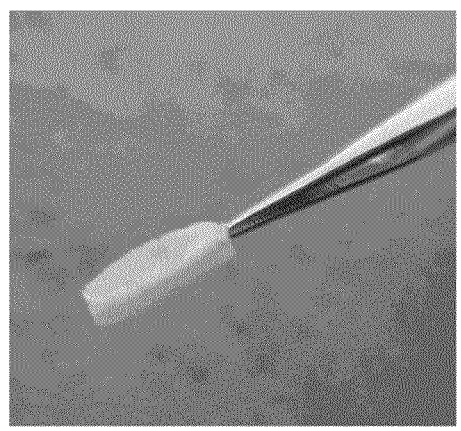

FIG. 5: Microscopic image of the three-dimensional biomaterial

This image shows the macroscopic three-dimensional structure of the solid biomaterial of the invention after lyophilization for which a standard 24-well culture plate was used as a mold. The image corresponds to the amount of biomaterial solidified in a well.

DETAILED DESCRIPTION OF THE INVENTION

The umbilical cord contains large amounts of (sulfated and non-sulfated) GAGs forming part of the soft connective tissue referred to as WJ. Among these GAGs, the main non-sulfated GAG is hyaluronic acid (Hadidian et al., 1948; Jeanloz et al., 1950), although smaller proportions of sulfated GAGs are also detected (Danishefsky et al., 1966). Furthermore, histological studies of the umbilical cord have suggested the presence of heparin (Moore et al., 1957). It is also very probable that the umbilical cord has more minor sulfated GAGs that have not been recognized yet.

The invention described herein is a hydrogel made up of GAGs obtained exclusively from the WJ of the umbilical cord. This hydrogel is completely free of the cells present in the WJ of the human umbilical cord from which the biomaterial is obtained, so it has no immunogenic components.

The biomaterial is formed by a mixture of glycosaminoglycans selected from the group comprising: hyaluronic acid, keratan sulfate, chondroitin-6-sulfate, heparan sulfate, chondroitin-4-sulfate, dermatan sulfate and heparin.

The biomaterial is preferably found forming the following combination and proportion of the mixture of GAGs: hyaluronic acid (65-75%), keratan sulfate (5-15%), chondroitin-6-sulfate (6-8%), heparan sulfate (3-7%), chondroitin-4-sulfate (2-6%), dermatan sulfate (1-5%) and heparin (0.1-2%), more preferably the combination of GAGs is: hyaluronic acid (70%), keratan sulfate (10%), chondroitin-6-sulfate (7%), heparan sulfate (5%), chondroitin-4-sulfate (4%), dermatan sulfate (3%) and heparin (1%).

The present invention also relates to the biomaterial made up of the previously described hydrogel, which optionally contains cells. The action of the hydrogel is thus enhanced in the regenerative and tissue repair process in severely damaged tissues or in tissues without the possibility of in situ cell replenishment by the patient, as a result of the fact that the biomaterial has healthy cells of the same type as the affected tissue. The cells contained in the biomaterial can be, among others: undifferentiated mesenchymal stem cells or mesenchymal stem cells differentiated into another cell strain, stem cells undifferentiated hematopoietic stem cells or hematopoietic stem cells differentiated into another cell strain, chondrocytes and chondroblasts, osteoblasts and osteocytes, keratinocytes, fibroblasts, myocytes, adipocytes, neurons or other cells from the nervous system, cells from the white blood cell system, corneal cells, endothelial cells or epithelial cells.

The present invention is divided into the following sections: (i) obtaining an extract of GAGs from Wharton's jelly of the umbilical cord (ii) production of a hydrogel from the GAGs isolated from Wharton's jelly of the umbilical cord (iii) characterizing the hydrogel obtained and (iv) uses of the biomaterial.

Obtaining an Extract of GAGs from the WJ of the Umbilical Cord

The process for obtaining the biomaterial comprises the following steps:
a. Obtaining a human umbilical cord;
b. Treating the umbilical cord with a saline solution and antibiotics;
c. Eliminating all the blood from the surface of the cord;
d. Fragmenting the cord into sections of 1-2 cm;
e. Cleaning out all the blood retained inside;
f. Eliminating the umbilical cord membrane and blood vessels;
g. Separating the gelatinous substance comprising Wharton's jelly;
h. Enzymatically digesting the gelatinous substance obtained; and
i. Precipitating and isolating the GAGs;

Specifically, the following is performed for isolating the glycosaminoglycans from the WJ of the umbilical cord:

Obtaining Wharton's Jelly

The umbilical cord is collected immediately after the delivery and it is processed or maintained at 4° C. until processing, and not more than 24 hours in these conditions should elapse.

For processing, the umbilical cord is preferably maintained in sterile conditions in a biosafety level II laminar flow hood. It is subjected to at least three successive washings with a DMEM (Dulbecco's Modified Eagle's Medium) solution or with phosphate buffer 1×(1×PBS) with a mixture of antibiotics (penicillin, streptomycin, amphotericin-B) and/or an erythrocyte lysis buffer solution, to completely remove blood residues.

Once the surface of the umbilical cord is cleaned of blood, it is transferred to a Petri dish and fragmented into sections of 1-2 cm. When cutting the cord into fragments it is possible that blood retained inside the blood vessels of the umbilical cord is released, so it will be necessary in this case to thoroughly clean the cord fragments.

The umbilical cord has at the structural level two umbilical arteries and one umbilical vein, sustained by a consistent matrix which is WJ and covered with a thin membrane. In order to exclusively obtain the WJ, the membrane and blood vessels are mechanically removed. To do so, the umbilical cord fragments are longitudinally sectioned and with the aid of a scalpel and tweezers both the umbilical cord membrane and blood vessels are carefully removed. The gelatinous substance that is obtained as a consequence of this mechanical separation is the WJ. Generally between 20 and 160 g of Wharton's jelly are obtained from 25 to 200 g umbilical cord.

Extraction of GAGs from Wharton's jelly

The protocol described in the literature (Rogers et al., 2006) for obtaining GAGs from human cartilage by means of enzymatic digestion with the enzyme papain (SIGMA, Ref: P-4762) was used, with some modifications, to obtain GAGs from the WJ of the umbilical cord.

The WJ obtained in the previous point is immersed in 10 ml of the extraction buffer solution (5 mM L-cysteine, 100 mM $Na_2HPO_4$ buffer solution, 5 mM EDTA, 10 mg (14 U/mg) papain, pH 7.5) for 24-48 hours at 60° C. for complete digestion.

Once the WJ has been entirely digested, it is centrifuged to remove the useless digestion residue. At this point, it is observed that the digestion volume is greater than the starting volume. This increase is due to the dissolution of the GAGs present in the WJ and therefore to the release of the water that they accumulate.

Once the sample is centrifuged, the supernatant is transferred to another container and the GAGs present in the sample are then precipitated out.

Precipitation and Isolation of GAGs from the WJ of the Umbilical Cord.

The GAGs of the WJ are precipitated out with 5 volumes of 100% ethanol. By means of this step, the GAGs of the sample as well as the salts present therein are precipitated out. The precipitation occurs due to the fact that the water molecules present in the sample interact with the ethanol molecules, such that the water molecules cannot interact with the GAGs of the sample, the latter becoming insoluble in water, and therefore precipitating out. Therefore, right after adding the ethanol and shaking the tube, a whitish precipitate is observed. The GAGs are left to precipitate for 12 hours at −20° C. Once precipitated out, they are centrifuged to remove the 100% ethanol and the precipitate is washed with 5 volumes of 75% ethanol to remove the possible residual salts that have precipitated out in the sample. The sample is centrifuged once again to completely remove the supernatant.

Once the sample of GAGs has precipitated, the solid residue is left to dry for at least 30 minutes at ambient temperature until all the ethanol has evaporated. Once the ethanol has evaporated, the sample of GAGs is resuspended in Milli-Q $H_2O$ and is stored indefinitely at 4° C.

The mechanical resistance of this type of material is low; they are not considered for bearing loads unless they are combined with another type of composite or calcium phosphate-type materials, but rather for performing a regenerative bioactive action in the damaged area. However, the greatest affinity between the polysaccharide molecules making up this hydrogel make them maintain a high cohesion with respect to one another, remaining in the injection site and having an adhesive nature.

Crosslinking: Obtaining Hydrogel

There are other therapeutic applications which require a more resistant and permanent biomaterial with an internal structure that allows its colonization by cells from either the adjacent tissues in the application site or by cells arranged in the biomaterial prior to its implantation. In this case, the biomaterial of the invention would act like a bioactive three-dimensional matrix to induce healing and repair of a tissue wound.

Hyaluronic acid, chondroitin-6- and -4-sulfate, keratan sulfate, dermatan sulfate, heparan sulfate and heparin regulate cell activity and activate the synthesis of a new extracellular matrix. The diversity of GAGs present in the biomaterial allows the existence of a number of binding sites specific to growth factors regulating the cell proliferation and differentiation processes, as well as the cells' capacity for the synthesis of a new extracellular matrix and growth factors. This effect causes a greater response capacity in the affected tissues and accelerates regeneration and even allows healing in the case of extremely degraded areas, as is the case of chronic ulcers.

In order for the biomaterial to be able to be used as a three-dimensional matrix, the extract of GAGs has to be stabilized, increasing its mechanical properties and allowing the formation of a three-dimensional structure. In order to achieve these objectives, the GAGs can be chemically modified or crosslinked to form a material in the form of a solid hydrogel. These chemical modifications typically involve alcohol or carboxylic groups.

For obtaining a stable and solid hydrogel, it is necessary to subject the sample to a crosslinking reaction (crosslinking, polymerization). This process involves the chains of a water-soluble polymer becoming insoluble (Elisseeff et al., 2005).

The hydrogels obtained by means of the crosslinking have unique properties making them potentially useful for tissue engineering: high water content for carrying nutrients or waste substances, elasticity and the capacity of encapsulating or immobilizing cells in situ in a 3D microenvironment. The crosslinking density directly affects the size of the pore of the hydrogel and therefore the physical properties thereof, such as the water content or the mechanical resistance for example. A hydrogel with a large crosslinking density and therefore a very small pore size will thus absorb less water and will have greater mechanical resistance than a hydrogel with a lower degree of crosslinking and a large pore size.

The formation of a hydrogel by crosslinking can be carried out by means of several methods: temperature changes, chemical reactions and photopolymerization.

In the present invention the crosslinking reaction is carried out as follows: an aqueous solution of the polymer to be crosslinked (in this case, an aqueous solution of GAGs) is obtained and the chemical reagent that will cause the crosslinking is added. In this case, to develop the hydrogel EDC (1-ethyl-3-(3-dimethylaminopropyl carbodiimide hydrochloride) is used because EDC activates carboxyl groups in aqueous solutions. These activated carboxyl groups are capable of reacting with primary amines or hydroxyl groups, resulting in amide or ester bonds. Once the hydrogel is formed, it is washed several times with PBS to remove the EDC residues that may remain. The GAG molecules are thus made to absorb large amounts of water, forming a hydrogel with a solid and porous aspect (Pieper et al., 1999; Wissink et al., 2001).

The hydrogel with a specific shape and size solidified during the crosslinking process in the mold intended for such purpose, such that it takes the desired shape and size depending on the mold that is used.

The solid hydrogels can be dried by means of the process referred to as lyophilization to thus obtain a porous structure due to the removal of the water molecules intercalated between the GAG molecules present in the hydrogel (FIG. 5). Furthermore, once the biomaterial is lyophilized, the three-dimensional structure of the hydrogel can be characterized by means of scanning electron microscopy (SEM) (FIG. 3). The solid hydrogel obtained is frozen by means of lyophilization and once frozen, it is introduced in a vacuum chamber in order to remove the water by the process referred to as sublimation. Virtually all the free water contained in the original hydrogel is removed by means of various freezing cycles.

Once the hydrogel is obtained in its final shape, it is sterilized by means of exposure to ultraviolet radiation for a period of 40 minutes. The sterility tests conducted on the hydrogel demonstrated that the biomaterial was optimally sterilized.

Once sterilized, the hydrogel is in the end product format, ready for its direct application or association with cells.

Cell association assays with the hydrogel of the invention proved that the biomaterial does not cause toxic effects on the cells, its proliferation capacity being similar to that occurring in standard culture conditions (FIG. 4).

Uses of the Biogel

The biomaterial of the invention, either in its form combined with cells or alone, can be applied in its injectable form in joint system diseases and in aesthetic treatments. The cells that can be used are, among others: undifferentiated mesenchymal stem cells or mesenchymal stem cells differentiated into another cell strain, undifferentiated hematopoietic stem cells or hematopoietic stem cells differentiated into another cell strain, chondrocytes and chondroblasts, osteoblasts and osteocytes, keratinocytes, fibroblasts, myocytes, adipocytes, neurons or other cells from the nervous system, cells from the white blood cell system, corneal cells, endothelial cells or epithelial cells.

Depending on the application for which the hydrogel will be intended, the injection technique will be different and the viscosity of the hydrogel will be adapted to the caliber of the injection system. The viscosity of the injectable hydrogel is from 10 to 15,000 cS, preferably between 10 and 2,000 cS. The crosslinked hydrogel can have a viscosity greater than 15,000 cS. The viscosity of the hydrogel can be modified by crosslinking according to needs, being able to obtain viscosities greater than 15,000 cS.

The biomaterial developed in the present invention can be applied preferably in injectable form in the following pathologies: remodeling, filling or reconstruction of soft tissues, the treatment of wrinkles, creases and scars, burns, ulcers, soft tissue augmentation, facial lipoatrophy, intervertebral disc diseases, repair of cartilage, musculoskeletal injuries, osteoarthritis and periarthritis; treatment of tumors, vaginal diseases, brain injuries, marrow repair, neurodegenerative disorders, cardiovascular diseases and lubricating processes, as an analgesic and anti-inflammatory.

The biomaterial of the invention in its solid form has a substantially porous structure. In said structure the pore diameter is 0.5-1,000 µm, preferably 0.5-500 µm, being able to have a viscosity greater than 15000 cS. Said biomaterial in its solid form can be applied preferably in the following pathologies: treatment of burns, ulcers and dermal-epidermal defects, treatment of opthalmological diseases, such as corneal injuries, retinal injuries or cataracts; repair of cartilage, treatment of the osteoarticular system, as in the case of osteochondral defects, osteoarthritis or bone defects, and an adjuvant in the resolution of vaginal diseases, treatment of gingivitis and periodontitis; use in the development of cell culture systems.

The chondral diseases are an important socio-economic problem worldwide. In this sense, despite the difficulty of recording their incidence, it is estimated that joint injuries affect 500 million people.

Chondral pathologies occur as a result of injuries or diseases which, if they are not treated, can result in degenerative diseases such as the osteoarthritis (OA).

OA is one of the most common types of arthritis which affects 35-40 million people in the United States and Europe. It is a degenerative disease which causes the disintegration of cartilage accompanied by a reaction in the bones. It generally affects hands, knees, hips feet and the neck, and in adults, it is considered one of the most common causes of physical incapacitation.

Joint cartilage is a highly specialized avascular tissue which protects the bone of the diarthrodial joint from forces associated with weight and impacts which lead to frictions between the joint surfaces. This tissue is formed by a single cell type, chondrocytes, and by an important and rich extracellular matrix. Said matrix consists of a dense network of type II collagen fibers (predominant molecule), and, within this network, macro-aggregates of proteoglycans, which contain GAGs such as chondroitin sulfate, keratan sulfate, hyaluronic acid and aggrecan.

The specialized architecture of cartilage and its limited repair capacity make the treatment of this type of injuries very complicated. The absence of vascularization makes its regenerative capacity very limited since the stem cells cannot access the damaged area to contribute in the regenerative process.

In recent years, biodegradable biomaterials have been used for the treatment of chondral injuries. In this sense, macroscopic synthetic polymers (lactic acid, glycolic acid, caprolactone . . . ) have become the most important and numerous group of biomaterials. However, these solid macroscopic materials require the use of aggressive surgical procedures, such as conventional surgery. For the purpose of overcoming these limitations, new biomatrixes that can be implanted by minimally invasive techniques, such as by injection or arthroscopy, are currently being developed.

Therefore, one of the applications of the injectable biomaterial of the present invention is the regeneration of the joint cartilage damaged the degenerative processes of osteoarthritis. Said biomaterial can be easily administered in the area to be regenerated by means of percutaneous techniques, such as arthroscopy or by means of any injection device. In addition to the easy administration, the injectable hydrogel has the property of forming a stable implant which is fitted to the size and geometry of the deteriorated tissue.

Another application of the biomaterial is the use of the three-dimensional biomaterial for the treatment of wounds.

Chronic diabetic, decubitus, and venous ulcers are an important problem that affects between 3 and 6 million people in the United States. This pathology affects 1-3% of the population of developed countries and 15% of the patients admitted in hospitals suffer this condition. The large number of patients suffering these injuries produces considerable socio-economic and healthcare repercussions, a high treatment cost thus being established, and the quality of life of the patient being considerably altered.

Ulcers are traumas that have a huge effect on the organism with a considerably complex physiopathology. A complex synergistic interaction occurs between fibroblasts (cells of the dermis), keratinocytes (cells of the epidermis), extracellular matrix and plasma-derived proteins occurs in the wound bed so that the different wound healing phases, hemostasis, inflammation, repair and remodeling, can occur.

However, the chronic nature and recurrence are the most relevant incidences in clinical progression. Despite the large variety of treatments and dressings available today, the healing percentage and healing rate continue to be extremely low being, therefore requiring more effective treatments that achieve fast wound healing. The progressive knowledge gained on the physiopathology of chronic ulcers in recent years has generated the development of new dressings that are a significant advancement in the treatment of this disease. Although until now, there is no ideal dressing for covering the skin; said dressing must comply with a series of basic characteristics such as fast adhesion to the wound, providing an effective barrier against the loss of liquids, resisting against mechanical pressures to provide long-term stability, they must be easy to sterilize, easy to handle and transport, and they must be innocuous.

The solid biomaterial of the invention has most of the characteristics necessary for a dressing to be effective in curing a chronic ulcer. In this sense, for the purpose of evaluating the therapeutic effect in chronic ulcers, the in vivo experimental study has been carried out using mice.

EXAMPLES

Example 1

Obtaining Wharton's Jelly

To isolate the GAGs from the WJ of the umbilical cord, the following was performed:

A 50 g umbilical cord was collected immediately after delivery in a sterile bottle in which 300 ml of PBS at 1× concentration (for 1 liter of $H_2O$: 8 g NaCl, 0.2 g KCl, 1.44 g $Na_2HPO_4$, 0.24 g $KH_2PO_4$, pH=7.4 in 1 L of $H_2O$) and 3 ml of a mixture of antibiotics of penicillin (30,000 units), streptomycin (30,000 μg) and amphotericin-B (75 μg) (LONZA, Ref: 17-745 E) at 1× concentration, had previously been deposited. The umbilical cord can be stored at 4° C. for not more than 24 hours until processing, but in this example the umbilical cord was processed immediately after it was received.

For processing, the umbilical cord was maintained in sterile conditions in a biosafety level II laminar flow hood and it was subjected to successive washings to completely remove the blood residues it contains. To that end, it was placed in a container and 300 ml of 1×PBS (for 1 liter of $H_2O$: 8 g NaCl, 0.2 g KCl, 1.44 g $Na_2HPO_4$, 0.24 g $KH_2PO_4$, pH=7.4 in 1 L of $H_2O$) containing 3 ml of a mixture of antibiotics of penicillin (30,000 units), streptomycin (30,000 μg) and amphotericin-B (75 μg) (LONZA, Ref: 17-745 E) were added; it was manually shaken by vertically tilting the bottle 5 times for 10 seconds, and the liquid was discarded, this operation being repeated at least 3 times until most of the blood was removed. Then the umbilical cord was washed with 500 ml of an erythrocyte lysis solution at 1× concentration (for 1 liter of $H_2O$: 8.99 g $NH_4Cl$, 1 g $KHCO_3$, 37 mg EDTA, pH 7.3) until the complete removal of blood residues.

Once the surface of the umbilical cord was cleaned of blood, it was transferred to a 10 cm Petri dish and was cut up with sterile scissors into 1-2 cm fragments. Since blood retained in the blood vessels was released while cutting the umbilical cord into fragments, 10 ml of 1×PBS containing 1 ml of a mixture of antibiotics (10,000 units), streptomycin (10,000 μg) and amphotericin-B (25 μg) were added to thoroughly clean said fragments, and the surface of the fragment was pressed against its support surface, making horizontal shifting movements along the fragment with a sterile scalpel. This process was repeated until all the blood residues were removed from the interior. The completely clean umbilical cord fragments were transferred to a sterile tube and were immediately processed, although if needed, they can be indefinitely cryopreserved at −80° C.

The membrane surrounding the umbilical cord and the blood vessels located therein was then mechanically removed. To do so, the pieces of umbilical cord were longitudinally opened and with the aid of a scalpel and tweezers both the umbilical cord membrane and blood vessels were carefully removed. The gelatinous substance that was obtained as a consequence of this mechanical separation is the WJ. 40 g of WJ were obtained.

Example 2

Extraction of GAGs from Wharton's Jelly

The protocol described to obtain GAGs from human cartilage was used, with some modifications, to obtain GAGs from the WJ of the umbilical (Rogers et al., 2006).

The WJ obtained in Example 1 was immersed in 10 ml of the extraction buffer solution (242 μl of 200 mM L-cysteine, 1.42 ml of 704 mM $Na_2HPO_4$ buffer, 100 μl of 0.5 M EDTA, 10 mg (14 U/mg), pH 7.5) papain (SIGMA, Ref: P-4762) and it was maintained at 60° C. for 24 hours to completely digest the WJ, and once it was digested, the sample was centrifuged at 800 rpm for 5 minutes to remove the digestion residue. It was observed that the digestion volume was 30 ml, approximately 20 ml more than the starting volume of 10 ml, due to the dissolution of the GAGs present in the WJ and therefore due to the release of the water these accumulated.

Once the sample was centrifuged, the supernatant was transferred to another tube and the GAGs present in the sample were then precipitated out.

Example 3

Precipitation and Isolation of GAGs from the WJ of the Umbilical Cord

The GAGs of the WJ present in the supernatant were precipitated out with 5 volumes of 100% ethanol. By means of this step, the GAGs of the sample as well as salts present therein were precipitated out. This is due to the fact that the water molecules present in the sample interact with the ethanol molecules, such that the water molecules cannot interact with the GAGs of the sample. The GAGs were left to precipitate for 12 hours at −20° C. Once precipitated out, they are centrifuged at 2500 rpm for 5 minutes, all the 100% ethanol thus being removed. The precipitate was washed with 5 volumes of 75% ethanol to remove the possible residual salts that may have precipitated out in the sample. Then it was centrifuged about 5 minutes at 2500 rpm and the supernatant was completely removed.

Once the sample has precipitated, the solid residue was left to dry for about 30 minutes at ambient temperature until all the ethanol had evaporated. The amount of GAGs that precipitate out starting from a sample of about 40 g of WJ can range between 50 and 300 mg, depending on the starting material. In this specific case, 200 mg GAG precipitate were obtained, which were resuspended in 2 ml of Milli-Q $H_2O$ and was thus kept stored at 4° C. until the hydrogel was produced.

Example 4

Production of an Injectable Hydrogel Containing GAGs of the WJ of the Umbilical Cord The water content of the hydrogel can be from 10% to 100 times its own weight, depending on the viscosity required for its application.

The hydrogel obtained after resuspension of the GAGs precipitated in 2 ml of $H_2O$ was resuspended in an injectable physiological serum solution to give a viscosity of 1000 cS. This hydrogel was subsequently resuspended in 8 ml of an injectable physiological serum solution to give a viscosity of 200 centistokes (cS) and was left stirring moderately in a vortex until complete dissolution and homogenization, to prevent the degradation of the structure of the gel.

Once the hydrogel was dissolved, it was stored at 4° C., where it can be kept indefinitely.

Example 5

Production of a Solid Hydrogel Containing GAGs from the WJ of the Umbilical Cord To produce the solid hydrogel, the process described in the literature was followed (Cui et al., 2006). An aqueous solution was prepared from the extract of GAGs obtained from the WJ according to Example 3. Specifically, a solution of GAGs in $H_2O$ at 1% was prepared. To that end, 10 ml of $H_2O$ were added to the 200 mg of GAGs obtained after their precipitation and isolation (Example 3). 1.2 g of adipic dihydrazide (ADH) were added to the solution and the pH of the solution was adjusted to pH=3.5 with 0.1 N HCl. Once this pH was adjusted, 0.6 g of the fixative, EDC (1-ethyl-3-(3-dimethylaminopropyl carbodiimide hydrochloride) (SIGMA, Ref: E6383), was added to the solution. The mixture was maintained between 30 minutes and 1 hour under constant stirring at ambient temperature until the solid hydrogel was obtained.

Once the solid hydrogel was formed, it was washed 3 times with 1×PBS (for 1 liter of $H_2O$: 8 g NaCl, 0.2 g KCl, 1.44 g $Na_2HPO_4$, 0.24 g $KH_2PO_4$, pH=7.4 in 1 L of $H_2O$) 5 minutes each time to remove the EDC excess. With respect to the physical shape of the hydrogel, it will have the shape of the mold in which it solidifies, such that standard 96, 48, 24, 12 and 6-well culture plates, Petri dishes or any other container with the desired shape can be used. Additionally, the hydrogel can be solidified in a large container such as a beaker, and once it is solidified, the hydrogel can be cut with characteristic shape and thickness. Specifically, in this example the hydrogel solidified in wells of 24-well plates and once solidified it was washed 3 times for 5 minutes with 500 μl of 1×PBS.

In this case, the solid hydrogel crosslinked in 24-well plates was subjected to the lyophilization process, which consists of the following steps: the hydrogel was frozen at −80° C. The frozen hydrogel samples were introduced in the vacuum chamber of the lyophilizer. The hydrogel samples were subjected to vacuum while the temperature was increased up to −40° C. at a rate of 0.1° C./minute and the temperature was maintained at −40° C. for 20 minutes. The temperature was subsequently increased to −20° C. at a rate of 0.1° C./minute and the temperature of −20° C. was maintained for 15 minutes. After this time, the temperature was increased to 0° C. at a rate of 0.1° C./minute and the temperature of 0° C. is maintained for 15 minutes. The temperature was subsequently increased to 25° C. at a rate of 0.1° C./minute and it was maintained at this temperature for the time necessary to equal the external pressure and the internal pressure of the vacuum chamber.

In this example, for the characterization three-dimensional of the hydrogel by means of scanning electron microscopy (SEM), once the hydrogel was lyophilized the following was performed: a section of the lyophilized hydrogel was cut and this section was dried to the critical point with $CO_2$ in an AUTOSAMDRI-814 dryer and metalized with gold in a SPUTTER. The preparations were observed at a voltage of 20 KV in the JEUL scanning electron microscope (JSM35).

The SEM analysis (FIG. 3) of the hydrogel indicated that it has a uniform porous structure and that it contains an interconnected network of pores. The micrograph shows the existence of a highly porous three-dimensional structure, with a pore diameter ranging between 0.5 and 500 μm. This range of pores involves the existence of micro- and macroporosity. The macropores (300-500 μm) are necessary so that suitable cell colonization is carried out, so that a high number of cells is concentrated and so that different cell types coexist, favoring the formation of structured tissues, for example, so that a vascular network can be formed. The intermediate pores allow cell integration. The micropores (0.5-50 μm) are necessary for cell survival, since they are responsible for carrying out the correct diffusion of gases, nutrients and the removal of the waste products resulting from cell metabolism. The pore size is measured based on the metric scale obtained by means of the scanning electron microscope.

In this case, unlike the previous example of the injectable biomaterial, the solid hydrogel provides a three-dimensional structure, which is a matrix for the cell growth and colonization in its entire structure, both internal and external. This biomaterial shows a higher structural sensitivity, being indicated for applications in which not only is a bioactive nature and trophic action sought, but also a structure which can temporarily house cells until the tissue repair is performed, such as the treatment of ulcers and other dermal-epidermal diseases, the repair of cartilage and opthalmological treatments, among others. The cells contained in the biomaterial can be those of the tissues adjacent to the implantation site which have managed to colonize it, or also cells arranged ex vivo in the biomaterial prior to its clinical application, such that its regenerative action is enhanced.

This biomaterial has a homogeneous distribution of pores with a size in a range of 0.01 a 500 microns, determined by means of scanning electron microscopy techniques. This porosity range is suitable both for the diffusion of gases and nutrients through its entire structure, and for allowing cells to enter it.

Example 6

Characterization and Quantification of GAGs Present in the Biomaterial of the Invention The different GAG present in the biomaterial of the invention were analyzed and quantified by means of the mass spectrometry (ESI/MS) technique. Given that by means of this technique only molecules with a molecular weight of between 200 and 2000 Daltons can be determined and that the GAG molecules exceed this range for the most part, first, the sample was enzymatically digested in order to thus obtain GAG chains with a molecular weight between 200 and 2000 Da.

As a standard for the identification and quantification of the GAGs, standard commercial compounds of each of them with a known concentration were used. Specifically, the standards used to perform the quantification of GAGs were the following: for hyaluronic acid: hyaluronic acid potassium salt (SIGMA, Ref: 53750); for chondroitin sulfate: chondroitin sulfate sodium salt (SIGMA, Ref: C4384); for dermatan sulfate: dermatan sulfate sodium salt (SIGMA, Ref: C3788); for keratan sulfate: keratan sulfate (CHEMOS, Ref: 7295); for heparin: heparin sodium salt (SIGMA, Ref: H8537); and for heparan sulfate: heparan sulfate sodium salt (SIGMA, Ref 51541).

The values of the quantification of GAGs present in the sample were obtained based on the results obtained for each GAG standard used.

In order to perform the enzymatic digestion of the GAGs, the process described in the literature was followed (Mahoney et al., 2001). To that end, the enzymes specific for the digestion of each GAG were used.

For hyaluronic acid, hyaluronidase (SIGMA, Ref: H3506) was used; for chondroitin sulfate, chondroitinase (SIGMA, Ref: C2780) was used; for dermatan sulfate, chondroitinase B (SIGMA, Ref: C8058) was used; for heparin, heparinase I (SIGMA, Ref: H2519) was used; for heparan sulfate, heparinase I (SIGMA, Ref: H2519) was used; for keratan sulfate, keratanase (K2876) was used.

These enzymes were prepared by resuspending 440 U of the corresponding enzyme in 10 ml of the following buffer: 2 ml of 100 mM phosphate buffer pH=7.77, 770 μl of 1 M NaCl, 1 mg of BSA and 7.23 ml of $H_2O$.

The enzymatic digestion buffer with an enzyme concentration of 160 U/ml was prepared as follows: 4.5 ml of enzyme (2000 U) were added to 7.5 ml of digestion buffer, 1.5 ml of 1 M NaCl, 0.333 ml of 3 M sodium acetate pH=5.2 and 5.67 ml of $H_2O$. The samples and the standards to be subjected to enzymatic digestion were prepared as follows: 500 μl of digestion buffer (80 U of enzyme) were added to 500 μl of standard for each GAG at a concentration of 2 mg/ml, such that the final solution of the standard was at a concentration of 1 mg/ml. The same was done with the sample of GAGs: 500 μl of digestion buffer (80 U of enzyme) were added to 500 μl of the sample of GAGs.

The samples were digested at 37° C. for 1 hour, after which the enzyme was inactivated by means of thermal denaturation at 60° C. for 5 minutes.

Once the digestions were done, the samples and the standards were analyzed by means of mass spectrometry. Mass spectrometry is an experimental methodology used to determine the mass-to-charge ratio of certain ions present in the sample to be analyzed. The mass spectrometer consists of 3 basic components: ion source, mass analyzer and detector. The sample to be analyzed is ionized by means of the ion sources, they are separated in the mass analyzer and are detected to produce a mass spectrum, in which the mass-to-charge values are shown compared to the relative abundance of a specific ion species.

Specifically, in this example the injection of samples in the mass spectrometer was carried out as follows: 20 μl of the samples were injected at a flow rate of 0.2 ml/minute directly into the mass/mass detector (Thermo LCQ model). The negative electrospray ionization (ESI −) method was used and the time of the chromatogram was set at 10 minutes. The molecular ions with a range of ±6 Da, corresponding, according to the literature (Mahoney et al., 2001), to the molecular weight of recognized chains for each type of GAG, were selected. Said ions remained present both in the sample of standard GAGs and in the sample to be analyzed, so the presence of each GAG in the sample was thus qualitatively demonstrated. To ensure the reproducibility of the results, the samples and the standards were injected in duplicate.

For the quantification of the different GAGs, a standard line was made for the standard for each GAG at 1 mg/ml. The standard line made consisted of the following concentrations of each of the standard GAGs (hyaluronic acid, chondroitin sulfate, dermatan sulfate, heparin, heparan sulfate and keratan sulfate) used to make the standard lines: 750 μg/ml, 500 μg/ml, 250 μg/ml, 100 μg/ml, 0 μg/ml. The dilutions of the standard line were carried out with $H_2O$ and a mixture containing equal proportions of enzymatic digestion buffer and $H_2O$ was used as the blank of the line.

Figure 1:
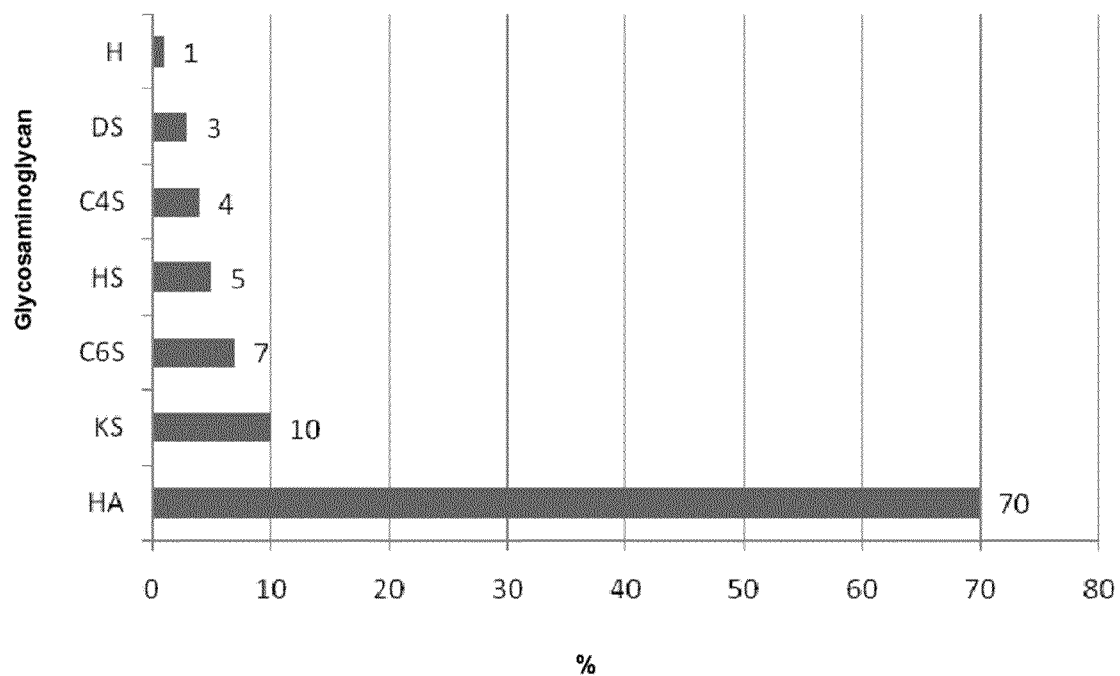
FIG. 1: Characterization and quantification of GAGs present in the biomaterial of the invention.

The results of the qualification and the proportions of each GAG in the biomaterial of the invention are the following, taking into account that the origin of the biomaterial is natural, which implies the existence of small variations in their composition (FIG. 1):

70% hyaluronic acid
10% keratan Sulfate
7% chondroitin-6-sulfate
5% heparan sulfate
4% chondroitin-4-sulfate
3% dermatan sulfate
1% heparin Example 7

Histological Study for Determining the Presence of Cell Rests in the Biomaterial The biomaterial of the invention contains a combination of GAGs of a natural origin. This natural origin enhances their regenerative effect and their effect on cell activity, since the structures of the GAGs and the interactions between them are similar to how they are found in the extracellular matrix in physiological conditions.

The umbilical cord is a type of tissue that is not very immunogenic, in fact, the heterologous use of the stem cells contained in the WJ is considered for treatments in a number of works. There are also works in which artery or vein systems are developed from the vasculature of the umbilical cord, also for heterologous use.

However, to ensure that the biomaterial of the invention is free of cells and of cell rests, which can cause inflammatory reactions or implant rejection reactions, hematoxylin-eosin, alcian blue and methyl green-pyronin histological stains have been performed (FIG. 2).

Hematoxylin-eosin: this is the histochemical stain most widely used on a histopathological level. It allows observing cells and cell components. Hematoxylin presents affinity for the acid components of the cell, especially nucleic acids, and eosin presents affinity for the basic areas, allowing a good observation of the cell cytoplasm. Preparations of the sample of GAGs (FIG. 2 B) were stained and extensions of cells were used as positive control (FIG. 2 A).

The process which was carried out to perform hematoxylin-eosin staining was the following: a sample of GAG was extended on a slide with the aid of a sterile swab, and the extension was left to dry at least 24 hours. Once the slides were dry, the extensions were fixed with 70% methanol for 5 minutes. After this time, the fixative was removed by washing with $H_2O$. The slides were stained with hematoxylin for 3 minutes (PANREAC, DC Harris hematoxylin solution). After this time, the excess dye was removed by washing with $H_2O$. All the slides were passed through $H_2O$ with 0.5% HCl to eliminate unspecific bonds of the dye. The slides were washed with $H_2O$. The slides were stained with eosin (0.5% in $H_2O$) for 30 seconds. The slides were washed with $H_2O$ to remove the eosin excess. Several drops of the Fluoromount-G mounting medium (SOUTHERN BIOTECH, Ref: 0100-01) were added to the preparation, they were covered with a slide cover and observed under a microscope.

The results of the stain with hematoxylin-eosin (FIG. 2, images A and B) indicate the absence of cells in the sample of analyzed GAGs.

Alcian blue: Alcian blue is one of the major cationic dyes (it contains positive charges in its molecule), which bind to sites with negative charges of the polysaccharides with sulfate, phosphate or carbonate radicals forming part of proteoglycans. These electrostatic bonds depend on the pH of the medium; at a neutral pH the dye binds to proteoglycans with neutral radicals; at acid pH it binds to sulfated proteoglycans; and at basic pH it binds to phosphate proteoglycans. At pH=1, alcian blue binds to weak and strongly sulfated proteoglycans, which contain chondroitin sulfate, dermatan sulfate, heparan sulfate and keratan sulfate forming part of the GAG of Wharton's jelly. Preparations of the sample of GAGs (FIG. 2 F) were stained and extensions of cells were used as control (FIG. 2 E).

The process that was carried out to perform the alcian blue staining in this example in particular was the following:

A sample of GAG was extended on a slide with the aid of a sterile swab, and the extension was left to dry at least 24 hours. Once the slides were dry, the extensions were fixed with 70% methanol for 5 minutes. After this time, the fixative was removed by washing with 1×PBS. The slides were immersed in 0.1 N HCl pH=1 for 5 minutes. After this time they were stained with 1% alcian blue in 0.1 N HCl pH=1 for 2 hours. The slides were immersed in 0.1 N HCl for 5 minutes and were immediately washed with $H_2O$ to remove the excess dye. Several drops of the Fluoromount-G mounting medium (SOUTHERN BIOTECH, Ref: 0100-01) were added to the preparations, they were covered with a slide cover and observed under a microscope.

The results of the stain with alcian blue (FIG. 2, images E and F) indicate the presence of GAGs in the analyzed sample of biomaterial.

Methyl green-pyronin: This stain is used for the histological investigation of the nucleic acid contained in tissues, as well as to demonstrate the presence of lymphatic cells and plasma cells. It is also useful in the identification of plasma cells and RNA in tissue sections and cytological preparations. The pyronin stains the cytoplasm of the plasma cells and most of the nucleoli red. The methyl green stains DNA a bluish-green (purplish) color. Preparations of the sample of GAGs were stained (FIG. 2 D) and extensions of cells were used as control (FIG. 2 C).

The process which was carried out to perform methyl green-pyronin staining in this example in particular was the following:

A sample of each GAG was extended on a slide with the aid of a sterile swab, and the extension was left to dry at least 24 hours. Once the slides were dry, the extensions were fixed with 70% methanol for 5 minutes. After this time, the fixative was removed by washing with $H_2O$. The slides were immersed in 0.1 N HCl pH=1 for 5 minutes. After this time they were stained with methyl green-pyronin for 5 minutes (0.012% methyl green in $H_2O$, 0.01% pyronin in $H_2O$, 0.75% methanol) and were immediately washed with $H_2O$ to remove the excess dye. Several drops of the Fluoromount-G mounting medium (SOUTHERN BIOTECH, Ref: 0100-01) were added to the preparations, they were covered with a slide cover and observed under a microscope.

The results of the stain with methyl green-pyronin (FIG. 2, images C and D) indicate the absence of nucleic acids in the analyzed sample of GAGs.

As can be seen in the images of FIG. 4, neither cells nor nucleic acid remains can be seen in the material of the invention. However, the presence of GAGs can be observed in the developed biomaterial by means of alcian blue staining.

Example 8

Toxicity of Several Cell Types on the Biomaterial of the Invention

The main requirement for a biomaterial to be able to be used for implantation or as a matrix for tissue engineering is the complete absence of cytotoxicity.

In order to verify that the biomaterial of the invention does not cause toxic effects, the cytotoxicity was determined by means of the MTT method (Roche Diagnostics), validated by the ECVAM (European Centre for the Validation of Alternative Methods) on the cells arranged on the biomaterial of the invention. The cell types used are associated with the pathologies at which the biomaterial is targeted, such as, skin keratinocytes and fibroblasts, bone osteoblasts, cartilage chondrocytes and adipose-derived mesenchymal stem cells, as well as the cell line indicated in ISO 10993 for L929 toxicity assays.

The assay MTT is based on the capacity of the mitochondrial enzymes of the live cells to transform certain substrates into other secondary metabolites. The amount of compound formed depends on the activity of the mitochondrial dehydrogenase, which is a clear indicator of the number of viable cells existing in the culture.

Specifically, this mitochondrial test, Cell Proliferation Kit I (MTT) Cat. No. 1 465 007 Roche, determines the transformation carried out by the cell mitochondrial dehydrogenase succinates of (yellow) tetrazolium salt into insoluble (blue) formazan crystals. The cells were subsequently permeabilized and the crystals formed are solubilized, leading to a colored solution that can be quantified by measuring its absorbance in an ELISA microplate reader at a wavelength of 550 nm. The results obtained are shown in FIG. 4.

The process to be followed is the following:

1. The cells were seeded in anti-adherent 96-well plates with 50 µl of biomaterial in each well at a density of 2000-5000 cells/well depending on the cell type. The suitable cell concentration for each cell type has been previously determined. The fibroblasts, osteoblasts, chondrocytes and adipose-derived mesenchymal stem cells, all from a primary culture of human origin, were seeded at a concentration of 4000 cells per well, the L929 mouse fibroblast line was seeded at a concentration of 200 cells per well and the keratinocytes obtained from human skin in primary culture were seeded at a concentration of 5000 cells per well.

2. The culture was left to stabilize at 37° C. and 5% $CO_2$ for 24 hours before initiating the cytotoxicity assays. This assay included positive controls (cells+medium+known material which induces cytotoxicity, in this case polyvinyl polychloride or PVC was used), control (cells+standard culture medium), and cells in contact with the biomaterial of the invention.

3. They were left incubating at 37° C. in the incubator for the time period indicated in the protocol until conducting the determinations, which in this case were at 24, 48 and 72 hours of contact.

4. After the incubation period ended, 10 µl of the MTT solution (0.5 mg/ml) were added to the culture in each well for each 100 µl of medium, and it was incubated for 4 hours at 37° C. in the incubator.

5. After incubation ended, the formazan crystals inside the cells can be observed. 100 µl of the solubilizing solution is added to each culture or well and it is incubated at 37° C. in the incubator overnight. The cells are thus permeabilized and the crystals thus solubilized with the 100 µl of solubilizer as indicated, leading to a readily quantifiable colored solution.

6. Once the crystals are solubilized, the culture plate is read directly with an ELISA reader at 550 nm. Before the reading, it is advisable to clean the lower surface of the plate with ethanol.

As can be observed in FIG. 4, the biomaterial of the invention did not cause toxic effects on any of the tested cell lines, there being no significant differences with respect to the control.

Example 9

Use of the Biomaterial of the Invention in its Injectable Form for the Treatment of Osteoarthritis For the in vivo evaluation of the therapeutic effect of the biomaterial of the invention in OA, the hydrogel obtained in Example 3 was used and it was resuspended in 8 ml of an injectable physiological serum solution to give a viscosity of 200 cS. Rabbits that were subjected to resection of the anterior cruciate ligament in one of their knees were used as an experimental model. This resection of the ligament was done by means of lateral arthrotomy. Next, for the purpose of destabilizing the knee, a period ranging from months to weeks was waited, during which time erosions in the cartilage similar to osteoarthritis occurred. In addition, animals without arthrotomy in the knee were used as a control group.

The wounded joint surface was prepared by means of washing and debridement by arthroscopic surgery and the injuries were covered with the injectable biomaterial of the invention. Four weeks after depositing the biomaterial, the animals were sacrificed and the cartilage was extracted. The cartilage obtained was fixed in 4% paraformaldehyde for its subsequent histological processing. To obtain the histological sections, the sample was included in paraffin, for which purpose it was maintained for 5 minutes in alcohols at 50, 70, 90 and 100%. The samples were subsequently placed in citrosol for 5 minutes and were included in paraffin until obtaining a solid block. 5 µm histological sections were obtained using a microtome, and the histological staining and immunolabeling were performed using these sections.

Different markers of the extracellular matrix of the cartilage were analyzed in the histological sections by means of immunohistochemical techniques. The specific molecules of the extracellular matrix of the cartilage and molecular markers studied were type II collagen, keratan sulfate, chondroitin-4-sulfate and chondroitin-6-sulfate. The immunolabeling was performed using monoclonal antibodies. The technique used for labeling the tissue section was direct immunolabeling, using monoclonal antibodies labeled with a fluorochrome. The labeling was observed using confocal microscopy.

The results obtained demonstrated that the biomaterial induced the regeneration of the wounded cartilage since:

The injectable biomaterial did not cause toxicity once implanted, i.e., inflammation phenomena were not observed at the macroscopic or microscopic level in the histological sections.

The biomaterial fit the geometry and size of the wound to be repaired and stayed in the area of the implantation.

Alterations in the phenotype of the cells of the healthy tissue next to the area of the implant were not observed.

The presence of extracellular matrix molecules specific for cartilage, such as type II collagen, in the area of the implant indicated the start of the regenerative process with the formation of new extracellular matrix of the same quality as that of the native tissue.

The presence of chondrocytes was observed in the area of the implant, which indicated the stimulation of cell migration, adhesion and proliferation.

These facts prove that the biomaterial of the invention promotes the regeneration of the chondral defect, unlike in the control animals which did not present any sign of cartilage repair.

Example 10

Use of the Three-Dimensional Biomaterial

The solid biomaterial of the invention obtained in Example 5 has most of the characteristics necessary for a dressing to be effective in curing a chronic ulcer. In this sense, for the purpose of evaluating the therapeutic effect in chronic ulcers, the in vivo experimental study has been carried out using Swiss albino mice that were subjected to a thermal abrasion of about 3 cm$^2$ in the dorsal area. Animals subjected to this same type of wound but which were treated with a commercial hyaluronic acid gel were used as control group.

For the application of the biomaterial of the invention, the surface of the induced wound was prepared by means of washing, disinfection and surgical debridement, and the injuries were covered and filled both in depth and superficially with the moldable solid biomaterial of the invention. 15 days after placing the biomaterial, the animals were sacrificed and the area of the wound was extirpated and fixed in 4% paraformaldehyde for its subsequent histological examination. For the processing, the sample was included in paraffin, for which purpose it was maintained for 5 minutes in alcohols at 50, 70, 90 and 100%. The samples were subsequently placed in citrosol for 5 minutes and were included in paraffin until obtaining a solid block. 5 μm histological sections were obtained using a microtome, and the histological staining and immunolabeling were performed using these sections.

Different epidermal phenotype markers, such as 5 and 10 keratin, differentiation markers, such as involucrin and loricrin, the dermal marker vimentin, and components of the matrix such as laminin, were analyzed in the histological sections by means of immunohistochemical techniques. The technique used for labeling the tissue section was direct immunolabeling, using monoclonal antibodies labeled with a fluorochrome. The labeling was observed using confocal microscopy.

The results obtained demonstrated that the biomaterial was effective in the regeneration of the ulcer since:

The biomaterial applied in the wound was immunologically inert and no signs of toxicity were presented.

The biomaterial fit the geometry and size of the wound to be repaired, completely covering the affected area both in depth and superficially.

The biomaterial promoted the hemostatic phenomenon, which is a sign of the start of the healing process.

As the healing process progresses, the biomaterial degraded and was replaced with dermal-epithelial components.

The histological sections showed that the biomaterial induced the migration and proliferation of fibroblasts and keratinocytes, which remained viable therein.

The biomaterial of the invention induced healing of the wound that was twice as effective with respect to the control animals, and furthermore the quality of the new scar tissue was significantly greater than that in the animals without the application of the biomaterial of the invention.

REFERENCES

Collins M. N, Birkinshaw C. 2008. "Physical properties of crosslinked hyaluronic acid hydrogels". Journal of Material Science. Materials in Medicine, 19: 3335-3343.

Coburn J. A, Pandit A. 2007. "Development of naturally-derived biomaterials and optimization of their biomechanical properties". Topics in Tissue Engineering, 3: 1-14.

Cui F. Z, Tian W. M, Hou S. P, Xu Q. Y, Lee I. S. 2006. "Hyaluronic acid hydrogel immobilized with RGD peptides for brain tissue engineering". Journal of Material Science. Materials in Medicine, 17: 1393-1401.

Danishefsky I, Bella Jr. A. 1996. "The sulfated mucopolysaccharides from human umbilical cord", J. of Biological Chemistry, 241: 143-146.

Dawson J. I, Oreffo R. 2008. "Bringing the regeneration gap: stem cells, biomaterials, and clinical translation in bone tissue engineering". Archives of Biochemistry and Biophysics, 473: 124-131.

Elisseeff J, Ruffner M, Kim T. G, Williams C. 2005. "Cellular photoencapsulation in hydrogels". Culture of Cells for Tissue Engineering, Chapter 9.

Goa K. L, Benfield P. 1994. "Hyaluronic acid. A review of its pharmacology and use as a surgical aid in ophthalmology, and its therapeutic potential in joint disease and wound healing." Drugs, 47: 536-566.

Gogiel T, Galewska Z, Jaworski S. 2005. "Pre-eclampsia-associated alterations in Wharton's jelly proteoglycans". Acta Biochim Pol, 52: 501-507.

Hadidian Z, Pirie N. W. 1948. "The preparation and some properties of hyaluronic acid from human umbilical cord". The Biochemical Journal, 42: 260-265.

Hiles M, Hodde J. 2006. "Tissue engineering a clinically useful extracellular matrix biomaterial". Int Urogynecol Journal, 17: 39-43.

Ishihara M, Obara K, Ishizuka T, Fujita M, Sato M, Masuoka K, SAITO Y, Yura H, Matsui T, Hattori H, Kikuchi M, Kurita A. 2002. "Controlled release of fibroblasts growth factors and heparin from photocrosslinked chitosan hydrogels and subsequent effect on in vivo vascularization". Journal of Biomedical Materials Research, 78: 364-371.

Jeanloz R. W, Forchielli E. 1950. "Studies on hyaluronic acid and related substances I. Preparation of hyaluronic acid and derivatives from human umbilical cord". Journal of Biological Chemistry, 186: 495-511.

Kanematsu A, Yamamoto S, Ozeki M, Noguchi T, Kanatani I, Ogawa O, Tabata Y. 2003. "Collagenous matrices as release carriers of exogenous growth factors". Biomaterials, 25: 4513-4520.

Laurent T. C, Fraser J. R. E. 1992. "Hyaluronan". The FASEB Journal, 6: 2397-2404

Longaker M, Chiu E. S, Harrison M. R, Crombleholme, Langer J. C, Duncan B. W, Adzick N. S, Verrier E. D, Stern R. 1989. "Studies in fetal wound healing" Annals of Surgery, 210: 667-672.

Mahoney D. J, Aplin R. T, Calabro A, Hascall V. C, Day A. J. 2001. "Novel methods for the preparation and characterization of hyaluronan oligosaccharides of defined length". Glycobiology, 11: 1025-1033.

Malkowski A, Sobolewski K, Jaworski S, Bankowski E. 2007. "FGF binding by extracellular matrix components of Wharton's jelly". Acta Biochim Pol, 54: 357-363.

Moore R. D, Schoenberg M. D. 1957. "Studies on connective tissue. I. The polysaccharides of the human umbilical cord". A. M. A. Archives of pathology, 64: 39-45.

Pieper J. S, Oosterhof A, Dijkstra P. J, Veerkamp J. H, van Kuppevelt T. H. 1999. "Preparation and characterization of porous crosslinked collagenous matrices containing bioavailable chondroitin sulphate", Biomaterials, 20: 847-858.

Rabenstein D. L. 2002. "Heparin and heparin sulfate: structure and function". Natural products reports, 19: 312-331.

Rogers B. A, Murphy C. L, Cannon S. R, and Briggs T. W. R. 2006. "Topographical variation in glycosaminoglycan content in human articular cartilage". The Journal of Bone and Joint Surgery, 88: 1670-1674.

Sobolewski K, Malkowski A, Bankowski E, Jaworski S. 2005. "Wharton's jelly as a reservoir of peptide growth factors." Placenta, 26, 747-752.

Toole B. P. 2004. "Hyaluronan: from extracellular glue to pericellular cue". Nature Cancer Reviews, 4, 528-539.

Torres D. S, Freyman T. M, Yannas I. V, Spector M. 2000. "Tendon cell contraction of collagen-GAG matrices in vitro: effect of cross-linking. Biomaterials, 21, 607-619.

Trowbridge J. M, Gallo R. 2002. "Dermatan sulfate: new functions from an old glycosaminoglycan". Glycobiology, 12: 117-125.

Ueno N, Chakrabarti B, Garg H. G. Hyaluronic acid of human skin and post-burn scar: heterogeneity in primary structure and molecular weight". 1992. Biochem Int, 26: 787-796.

Wissink M. J. B, Beernink R, Pieper J. S, Poot A. A, Engbers G. H. M, Beugeling T, van Aken W. G, Feijen J. 2001. "Binding and release of basic fibroblast growth factor from heparinized collagen matrices", Biomaterials, 22: 2291-2299.

The invention claimed is:

1. A hydrogel biomaterial comprising:
   a) an extract of Wharton Jelly of human umbilical cord which consists of a mixture of GAGs (glycosaminoglycans) consisting of hyaluronic acid, keratan sulfate, chondroitin-6-sulfate, heparan sulfate, chondroitin-4-sulfate, dermatan sulfate and heparin, wherein said extract is free of human umbilical cord membrane, blood vessels, and cells originally present in the Wharton's Jelly; and
   b) cells that were not originally present in the Wharton's Jelly.

2. The hydrogel biomaterial of claim 1, comprising 65-75% hyaluronic acid of the total GAGs.

3. The hydrogel biomaterial of claim 1, comprising 5-15% keratan sulfate of the total GAGs.

4. The hydrogel biomaterial of claim 1, comprising 6-8% chondroitin-6-sulfate of the total GAGs.

5. The hydrogel biomaterial of claim 1, comprising 3-7% heparan sulfate of the total GAGs.

6. The hydrogel biomaterial of claim 1, comprising 2-6% chondroitin-4-sulfate of the total GAGs.

7. The hydrogel biomaterial of claim 1, comprising 1-5% dermatan sulfate of the total GAGs.

8. The hydrogel biomaterial of claim 1, comprising 0.1-2% heparin of the total GAGs.

9. The hydrogel biomaterial of claim 1, comprising 70% hyaluronic acid, 10% keratan sulfate, 7% chondroitin-6-sulfate, 5% heparan sulfate, 4% chondroitin-4-sulfate, 3% dermatan sulfate and 1% heparin.

10. The hydrogel biomaterial according to claim 1, having a viscosity of 10 to 15,000 cS.

11. The hydrogel biomaterial of claim 10, having a viscosity of between 10 and 2,000 cS.

12. A three dimensional structure comprising the hydrogel biomaterial of claim 1 wherein the extracted mixture of GAGs has been crossed-linked.

13. The three-dimensional structure of claim 12, having a viscosity of greater than 15,000 cS.

14. The three-dimensional structure of claim 13, having a substantially-porous structure with a pore diameter range of 0.5-1000 µm.

15. The three-dimensional structure of claim 14, having a pore diameter range of 0.5-500 µm.

16. The hydrogel biomaterial of claim 1 or 12, wherein said cells are selected from the group consisting of undifferentiated mesenchymal stem cells, mesenchymal stem cells differentiated into another cell strain, undifferentiated hematopoietic stem cells, hematopoietic stem cells differentiated into another cell strain, chondrocytes, chondroblasts, osteoblasts, osteocytes, keratinocytes, fibroblasts, myocytes, adipocytes, neurons, cells from the nervous system, cells from the white blood cell system, corneal cells, endothelial cells, and epithelial cells.

17. A process for obtaining the hydrogel biomaterial according to claim 1, characterized in that it comprises the following steps:
   a) Obtaining a human umbilical cord;
   b) Treating the umbilical cord with a saline solution and antibiotics;
   c) Eliminating all the blood from the surface of the cord;
   d) Fragmenting the cord into sections of 1-2 cm;
   e) Cleaning out all the blood retained inside;
   f) Eliminating the umbilical cord membrane and blood vessels;
   g) Separating the gelatinous substance comprising Wharton's jelly;
   h) Enzymatically digesting the gelatinous substance obtained; and
   i) Precipitating and isolating the GAGs, and resuspending the solid precipitate in water to obtain an aqueous extract consisting of a mixture of GAGs consisting of hyaluronic acid, keratan sulfate, chondroitin-6-sulfate, heparan sulfate, chondroitin-4-sulfate, dermatan sulfate and heparin, free of human umbilical cord membrane, blood vessels and cells present originally in Wharton Jelly;
   j) adding cells that were not originally present in the Wharton's Jelly.

18. The process according to claim 17, further comprising cross-linking the GAGs mixture obtained in step i).

19. The process according to claim 18, characterized in that the cross-linking is carried out by changes in temperature, chemical reactions or photopolymerization.

* * * * *